United States Patent [19]

Hattori et al.

[11] 4,324,218

[45] * Apr. 13, 1982

[54] AIR-FUEL RATIO DETECTING SYSTEM

[75] Inventors: Tadashi Hattori, Okazaki; Yoshiki Ueno, Aichul, both of Japan

[73] Assignee: Nippon Soken, Inc., Nishio, Japan

[*] Notice: The portion of the term of this patent subsequent to Dec. 9, 1997, has been disclaimed.

[21] Appl. No.: 199,922

[22] Filed: Oct. 23, 1980

Related U.S. Application Data

[63] Continuation of Ser. No. 18,776, Mar. 8, 1979, abandoned.

[30] Foreign Application Priority Data

May 30, 1978 [JP] Japan .................................. 53-64710
Jun. 14, 1978 [JP] Japan .................................. 53-71623

[51] Int. Cl.³ .......................... F02B 3/08; F02D 5/00
[52] U.S. Cl. .................................... 123/440; 123/489
[58] Field of Search .................. 123/440, 489; 60/276, 60/285

[56] References Cited

U.S. PATENT DOCUMENTS

| | | | |
|---|---|---|---|
| 4,140,085 | 2/1979 | Rabus et al. | 123/489 |
| 4,156,413 | 5/1979 | Taplin | 123/489 |
| 4,170,965 | 10/1979 | Aono | 123/440 |
| 4,171,690 | 10/1979 | Hosaka et al. | 123/440 |
| 4,237,839 | 12/1980 | Ueno et al. | 123/440 |

Primary Examiner—Raymond A. Nell
Attorney, Agent, or Firm—Cushman, Darby & Cushman

[57] ABSTRACT

An air-fuel ratio detecting system detects the air-fuel ratio of the mixture supplied to an engine by means of titania whose electric resistance value varies in response to the oxygen content of the exhaust gases. The titania is connected in series with a reference resistor and a fixed voltage is applied to the junction of the titania and the reference resistor so as to generate a voltage corresponding to a change in the electric resistance of the titania. The detection voltage generated at the junction indicates the air-fuel ratio of the mixture and it is compared with a reference voltage for determining whether the air-fuel ratio is equal to the stoichiometric air-fuel ratio. The electric resistance of the titania varies with its operating temperature and the detection voltage varies correspondingly. To prevent any error in the control of air-fuel ratio due to a change in the temperature-dependent detection voltage, the peak value of the detection voltage which indicates that the air-fuel ratio of the mixture is greater than the stoichiometric ratio is sampled and the reference voltage is changed in response to the peak voltage. A programmable read-only memory is used to allow easy setting of the peak voltage and the reference voltage in a nonlinear relation with each other.

18 Claims, 12 Drawing Figures

AIR-FUEL RATIO DETECTING SYSTEM

This is a continuation of application Ser. No. 18,776 filed Mar. 8, 1979, now abandoned.

BACKGROUND OF THE INVENTION

The present invention relates to air-fuel ratio detecting systems, and more particularly the invention relates to improvements in such systems designed to detect the air-fuel ratio of the mixture from the composition of the exhaust gases of an engine.

In the past, an air-fuel ratio detecting system of the type adapted to detect the air-fuel ratio A/F from the composition, e.g., the oxygen content of the exhaust gases from an engine has been proposed which includes an air-fuel ratio sensor principally composed of a metal oxide semiconductor such as titania ($TiO_2$) semiconductor and having an electric resistance value dependent on the oxygen content and a fixed resistor connected to the air-fuel ratio sensor, whereby the voltage generated at their junction is compared with a fixed reference voltage in a comparator circuit to detect whether the air-fuel ratio of the mixture is greater (oxygen is present in the exhaust gases) or smaller (oxygen is not present in the exhaust gases) than the stoichiometric air-fuel ratio.

A disadvantage of this type of system is that since the reference voltage is preset to a fixed value, if the electric resistance value Re characteristic of the air-fuel ratio sensor shifts on the whole due to the operating temperature or the change in the lapse of time, error will be caused in the detection of air-fuel ratio or the detection will be made impossible.

Figure 1A:
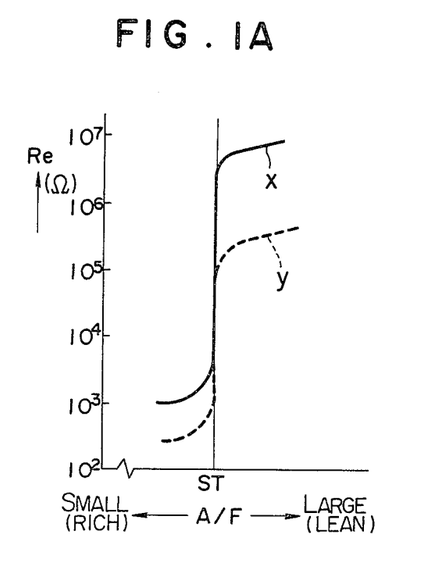
FIGS. 1A and 1B are graphs showing the electric resistance value characteristics of an air-fuel ratio sensor.
Figure 1B:
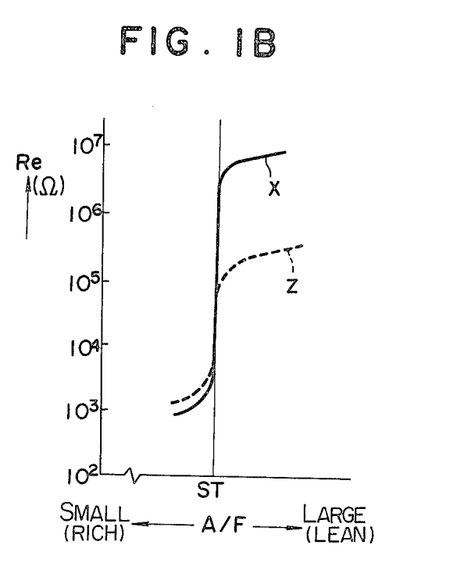

For instance, a brand-new air-fuel ratio sensor exhibits at an operating temperature of about 500° C. the characteristic shown by a curve x in FIG. 1A and the brand-new sensor shows at an operating temperature of about 800° C. the characteristic shown by a curve y in FIG. 1A, while after an endurance test the air-fuel ratio sensor exhibits at the same operating temperature of 500° C. the characteristic shown by a curve z in FIG. 1B.

Figures 2, 3, 4:
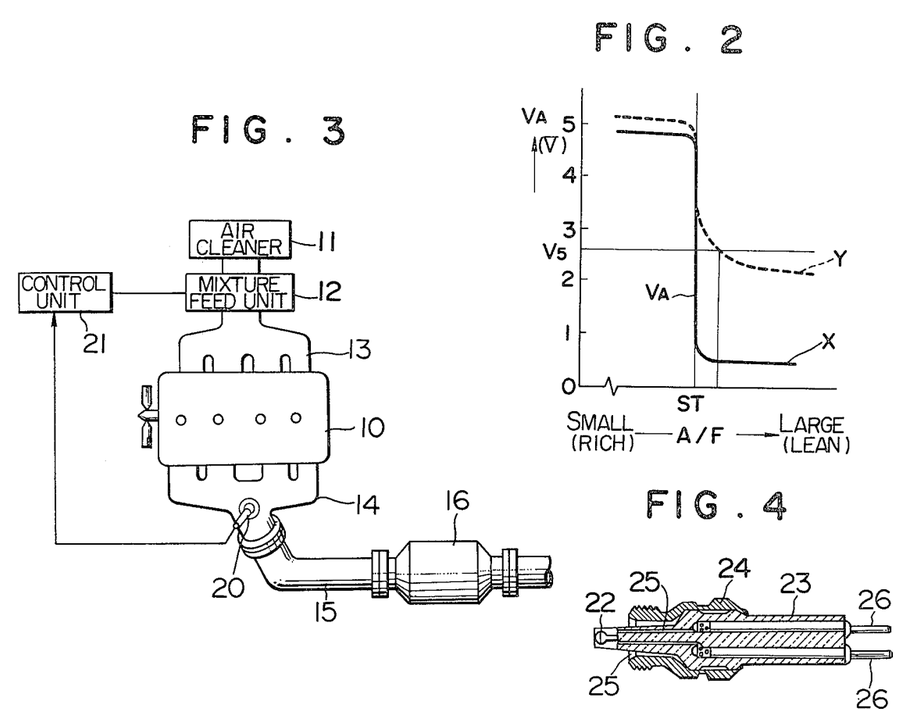
FIG. 2 is a graph showing the voltage at the junction point A.
FIG. 3 is a schematic diagram of an air-fuel ratio control system incorporating the invention.
FIG. 4 is a sectional view of the air-fuel ratio sensor shown in FIG. 3.

As a result, with the brand-new air-fuel ratio sensor used at a temperature of 500° C., a voltage $V_A$ at the junction of the sensor and the fixed resistor changes, as shown by a curve X in FIG. 2. Thus the point of intersection between the voltage $V_A$ and a reference voltage $V_S$, shown by a solid line, represents a stoichiometric air-fuel ratio ST, making it possible to satisfactorily detect whether the air-fuel ratio of the mixture is greater or smaller than the stoichiometric ratio ST.

However, when the electric resistance value characteristic of the air-fuel ratio sensor changes or shifts due to a change in the operating temperature or by the lapse of time, the voltage $V_A$ changes as for example shown by a curve Y in FIG. 2 and consequently the point of intersection between the voltage $V_A$ and the reference voltage $V_S$ deviates to the greater or lean side of the stoichiometric ratio ST, causing an error in the detection of air-fuel ratio A/F. In an extreme case, there no longer exists any point of intersection for the voltage $V_A$ and the reference voltage $V_S$, thus making the detection of air-fuel ratio impossible. In particular, as shown in FIG. 2, the voltage corresponding to the air-fuel ratio of mixtures changes very greatly with a change in the ambient temperature when the air-fuel ratio is greater than the stoichiometric ratio, although the voltage corresponding to the air-fuel ratio changes to a relatively small extent when the air-fuel ratio is smaller than the stoichiometric ratio.

SUMMARY OF THE INVENTION

It is an object of the invention to provide an air-fuel ratio detecting system which is capable of satisfactorily detecting the air-fuel ratio of mixtures despite variations in the operating temperature and lapse of time.

In accordance with the invention the above object is attained by sampling the peak value of an output voltage of an air-fuel ratio sensor which is indicative of a large air-fuel ratio, generating a reference voltage corresponding to the sampled peak value from a read-only memory into which a desired input-output relation has been preliminarily programmed and then comparing the output voltage of the air-fuel ratio sensor with the reference voltage.

DESCRIPTION OF THE PREFERRED EMBODIMENTS

The present invention will now be described with reference to the illustrated embodiments.

Referring to FIG. 3 showing a system incorporating the invention, the system will now be described with reference to the Figure. An engine 10 is a known type of spark ignition engine which uses gasoline or LPG as fuel and in which the intake system comprises an air cleaner 11, a mixture feed unit 12 and an intake manifold 13 and the exhaust system comprises an exhaust manifold 14, an exhaust pipe 15, an exhaust gas purifying three-way catalytic converter 16 and a muffler which is not shown.

The mixture feed unit 12 may comprise a carburetor or fuel injection system including a known type of electronic air-fuel ratio controller and the air-fuel ratio of a mixture produced (the intake system) is changed in response to an electric signal. The three-way catalytic converter 16 is of the type which is capable of simultaneously purifying $NO_x$, HC and CO with a high purifying percentage when the mixture of an air-fuel ratio which is around the stoichiometric ratio is supplied to the engine 10, and the converter 16 incorporates a known type of pellet type or honey-comb type catalyst.

Now referring to an air-fuel ratio detecting system, it comprises an air-fuel ratio sensor 20 mounted in the meeting place of the exhaust manifold 14 and a control unit 21 adapted to apply an electric signal to the mixture feed unit 12.

The air-fuel ratio sensor 20 is constructed as shown in FIG. 4. In the Figure, a disk element piece 22 whose electric resistance value varies in a step fashion in response to the gas composition, particularly the oxygen content of the exhaust gases, is composed of a metal oxide semiconductor such as a titania ($TiO_2$) semiconductor and it carries thereon a catalyst such as platinum (Pt), rhodium (Rh) or the like. The element piece 22 is held on the forward end of a heat resisting and electrically insulating holder 23 composed of a sintered material such as alumina. The holder 23 is coupled to a housing 24 made of a heat resisting metal and the sensor 20 is mounted to the exhaust manifold 14 by the threaded portion of the housing 24.

Two platinum electrodes 25 provided inside the holder 23 are inserted into the element piece 22, and each of the electrodes 25 is electrically connected to a terminal rod 26 through a conductive glass. The electric resistance value of the element piece 22 is taken out from the terminal rods 26.

The electric resistance value Re characteristic of the air-fuel ratio sensor 20 varies with variations in the operating temperature as shown in FIG. 1A and it also varies with aging as shown in FIG. 1B.

Next, the control unit 21 will be described with reference to FIG. 5. A power source 31 supplies a fixed DC voltage $V_P$ and its one end is connected to the air-fuel ratio sensor 20. A fixed resistor 32 is connected in series with the air-fuel ratio sensor 20 and a voltage $V_A$ responsive to variations of the air-fuel ratio A/F is generated from their junction A as shown by a curve $V_A$ in (a) of FIG. 6. The resistance value of the resistor 32 should preferably be determined according to the minimum temperature characteristic within the ordinary operating temperature range of the air-fuel ratio sensor 20, and the resistance value is selected $10^6$ ohms in this embodiment.

A comparator circuit 33 comprises input resistors 101 and 102 and a comparator 103, and the comparator 103 receives at its noninverting input terminal (+) the voltage $V_A$ generated at the junction A and at its inverting input terminal (−) a reference voltage $V_S$. The comparator 103 generates a "1" level rich signal when the voltage $V_A$ becomes higher than the reference voltage $V_S$ and the comparator 103 generates a "0" level lean signal when the voltage $V_A$ becomes lower than the reference voltage $V_S$.

A monostable multivibrator 34 generates a strobe signal of a pulse width $\tau$ in response to the positive-going transition or transition from the "0" level to the "1" level of the output signal of the comparator 103 in the comparator circuit 33.

A logical circuit 35 comprises an inverter 104 for inverting the output pulse signal of the monostable multivibrator 34 and an AND gate 105 for performing the AND logic operation on the output signals of the comparator 103 and the inverter 104, and the AND gate 105 generates a "1" level strobe signal when a "1" level signal and a "0" level signal are generated respectively from the comparator 103 and the monostable circuit 34.

A peak sample-and-hold circuit 36 comprises a buffer amplifier 106 consisting of a voltage follower, a diode 107, a capacitor 108 connected so as to be charged from the power source 31 and a semiconductor type analog switch 109 connected in parallel with the capacitor 108, whereby when the voltage $V_A$ at the junction A reaches a minimum peak value (indicative of an air-fuel ratio greater than the stoichiometric ratio), the voltage is detected and held.

The voltage $V_A$ at the junction A is applied to the noninverting input terminal (+) of the buffer amplifier 106 which in turn generates a voltage substantially equal to the voltage $V_A$. The on-off operations of the analog switch 109 are controlled by the output signal of the logical circuit 35 so that the analog switch 109 is turned on in response to the application of a "1" level signal and it is turned off in another condition.

Figure 7:
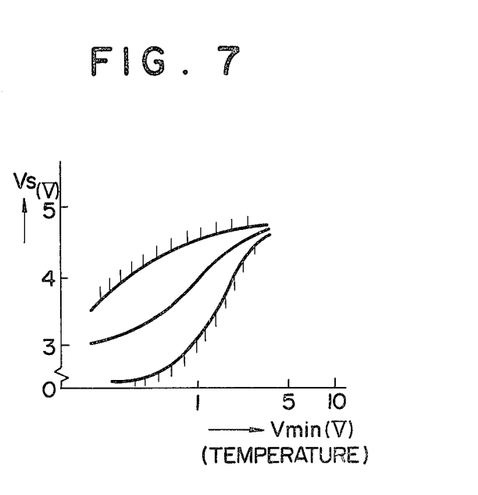

A voltage generating circuit 37 comprises an analog-to-digital converter 110 (hereinafter referred to as an A-D converter) for converting the analog output voltage of the peak hold circuit 36 to a binary digital signal, a latch circuit 111 responsive to the application of a "1" level pulse signal from the monostable multivibrator 34 to temporarily store the digital signal from the A-D converter 110, a read-only memory 112 (hereinafter referred to as a ROM) preliminarily programmed to generate a digital reference voltage having a nonlinear functional relation with respect to the digital signal from the latch circuit 111 as shown in FIG. 7 and a digital-to-analog converter 113 (hereinafter referred to as a D-A converter) for converting the digital reference voltage signal from the ROM 112 to an analog reference voltage $V_S$, and the output voltage of the D-A converter 113 is applied as a reference voltage $V_S$ to the comparator circuit 33.

With the construction described above, the electric resistance value of the air-fuel ratio sensor 20 varies in response to the gas composition or the oxygen content of the exhaust gases from the engine 10. The exhaust gas composition varies in response to the air-fuel ratio of the mixture supplied to the engine 10 from the mixture feed unit 12 and consequently the electric resistance value Re of the air-fuel ratio sensor 20 varies in response to the air-fuel ratio A/F as shown in FIG. 1.

Figure 6:
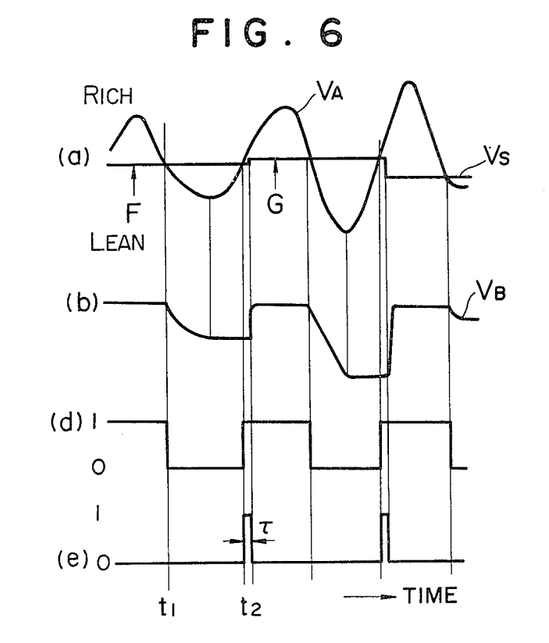
FIGS. 6 and 7 are graphs useful for explaining the operation of the first embodiment.

The voltage $V_A$ at the junction A is determined by the electric resistance value Re of the air-fuel ratio sensor 20 and the voltage $V_A$ varies with variations of the air-fuel ratio A/F as shown by the curve $V_A$ in (a) of FIG. 6.

When the reference voltage $V_S$ generated from the voltage generating circuit 37 is at the level shown at F in (a) of FIG. 6, as long as the voltage $V_A$ at the junction A is higher than the reference voltage $V_S$ the comparator circuit 33 generates a "1" level rich signal as shown in (d) of FIG. 6. When the voltage $V_A$ becomes lower than the reference voltage $V_S$ at a time $t_1$, the output of the comparator circuit 33 goes from the "1" level to the "0" level. As a result, the "0" level signal is applied to the AND gate 105 whose output signal also goes to the "0" level, with the result that the analog switch 109 is turned off and the capacitor 108 starts to charge.

Consequently, a voltage $V_B$ at a terminal B of the capacitor 108 decreases in response to the output voltage of the buffer amplifier 106 or the voltage $V_A$ at the junction A, so that when the voltage $V_B$ attains a minimum peak value, the minimum peak value is detected and held as shown in (b) of FIG. 6.

When the voltage $V_A$ becomes again higher than the reference voltage $V_S$ at a time $t_2$, the output of the comparator circuit 33 goes from the "0" level to the "1" level. In response to the transition of the signal, the monostable multivibrator 34 generates a "1" level strobe signal $\tau$ and the voltage $V_B$ at this time at the terminal B of the capacitor 108 is read through the A-D converter 110 by the latch circuit 111 which in turn stores the voltage temporarily.

This voltage value is modulated with the nonlinear functional relation shown in FIG. 7 and it is generated as a reference voltage value $V_S$ from the ROM 112. As a result, the new reference voltage $V_S$ is applied to the comparator circuit 33 through the D-A converter 113 and the reference voltage $V_S$ is changed to a level G in (a) of FIG. 6.

When the strobe signal of the monostable multivibrator 34 shown in (e) of FIG. 6 goes to the "0" level, a "1" level signal is applied to each of the two inputs of the AND gate 105 so that the AND gate 105 generates a "1" level signal and the analog switch 109 is turned on, thus discharging the charge on the capacitor 108. Thereafter, the respective circuits repeat the above-mentioned operations.

While the programmed output values of the ROM 111 are set in correspondence with variations in the resistance value of the air-fuel ratio sensor 20 as voltage variations, with the conversion of the electric resistance Re into the voltage $V_A$ the programmed output values are set in the nonlinear functional relation of FIG. 7 with the minimum peak values $V_{min}$ of the voltage $V_A$ and consequently the reference voltage $V_S$ decreases with a decrease in the minimum peak value $V_{min}$ of the voltage $V_A$ or a decrease in the ambient temperature.

As a result, when the operating temperature of the air-fuel ratio sensor 20 is 500° C., the voltage $V_A$ at the junction A changes in accordance with the change of the air-fuel ratio as shown by the curve X in FIG. 2 and the voltage $V_A$ intersects the reference voltage $V_S$ shown by the solid line at the stoichiometric air-fuel ratio ST. On the other hand, when the operating temperature rises to 800° C., when the air-fuel ratio sensor 20 is subjected to a reducing atmosphere for a long period of time or when the sensor 20 is deteriorated so that the voltage at the junction A varies as shown by the curve Y in FIG. 2 and the voltage value corresponding to the lean air-fuel ratio increases, the reference voltage $V_S$ increases correspondingly as shown by the dotted line in FIG. 2, and the curve Y and the reference voltage $V_S$ cross each other at the stoichiometric air-fuel ratio ST.

In other words, the voltage $V_A$ and the reference voltage $V_S$ cross each other at the stoichiometric air-fuel ratio ST irrespective of the overall variations of the electric resistance value Re due to the operating temperature, etc., of the air-fuel ratio sensor 20. It has been proved experimentally that in order that the voltage $V_A$ may cross the reference voltage $V_S$ at around the stoichiometric air-fuel ratio ST, it is necessary to set the values of the reference voltage $V_S$ to fall within the region enclosed by the hatching in FIG. 7. Therefore, the values of the reference voltage $V_S$ can be advantageously set by the ROM 111 which is programmable as desired. Since the comparator circuit 33 compares the voltage $V_A$ with the reference voltage $V_S$, when the comparator circuit 33 generates a "0" level air-fuel ratio detection signal it is an evident indication that the air-fuel ratio of the mixture is greater than the stoichiometric air-fuel ratio ST, and when a "1" level air-fuel ratio detection signal is generated it is an indication that the air-fuel ratio A/F is smaller than the stoichiometric ratio ST.

The air-fuel ratio detection signal is then applied to the mixture feed unit 12 through a drive circuit which is not shown, so that when the signal is at the "0" level, the air-fuel ratio adjuster of the mixture feed unit 12 enriches the mixture or make the mixture thick and the air-fuel ratio A/F is reduced, thus causing the air-fuel ratio A/F to approach the stoichiometric ratio ST.

On the other hand, when the air-fuel ratio detection signal goes to the "1" level, the air-fuel ratio adjuster of the mixture feed unit 12 leans out the mixture and the air-fuel ratio A/F is increased, thus causing the air-fuel ratio A/F to approach the stoichiometric ratio ST.

In this way the air-fuel ratio A/F is always controlled accurately at the stoichiometric air-fuel ratio ST and the three-way catalytic converter 16 purifies $NO_X$, HC and CO in the exhaust gases with a high purifying percentage.

Figure 8:
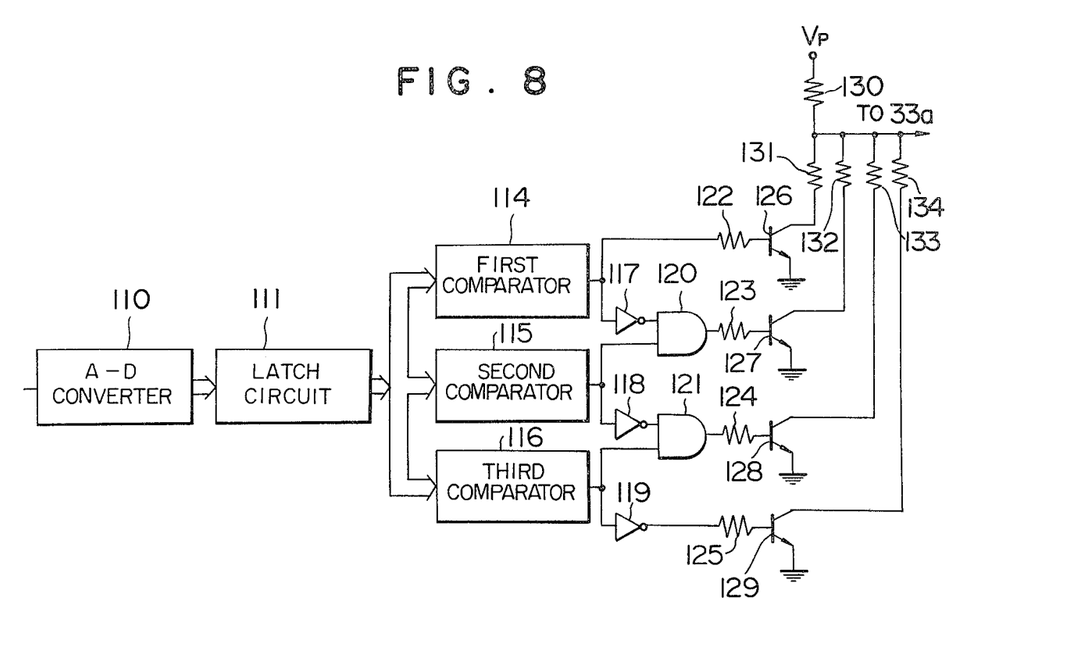
FIG. 8 is a circuit diagram showing the principal parts of a second embodiment of the invention.

While, in the above-described embodiment, the voltage generating circuit 37 includes the ROM 112 to generate a reference voltage $V_S$, the signal may be generated by means of a comparator as in the case of the second embodiment shown in FIG. 8. In the Figure a voltage generating circuit 37 comprises, in addition to an A-D converter 110 and a latch circuit 111, a first comparator 114, a second comparator 115, a third comparator 116, inverters 117, 118 and 119, AND gates 120 and 121, input resistors 122 to 125, transistors 126 to 129 and reference voltage adjusting resistors 130 to 134.

With this circuit, the first to third comparators 114 to 116 are all of the digitial type and a "1" level signal is generated when the binary output value of the latch circuit 111 exceeds first, second and third preset values $S_1$, $S_2$ and $S_3$, respectively (when $S_1 > S_2 > S_3$). As a result, when the output value of the latch circuit 111 is below the preset value $S_3$, all the comparators 114 to 116 generate a "0" level signal so that only the transistor 129 is turned on and a voltage $V_4$ produced by dividing a power supply voltage $V_P$ through the resistors 130 and 134 is generated as the required reference voltage $V_S$.

When the output value of the latch circuit 111 assumes a value intermediate of the preset values $S_2$ and $S_3$, the comparators 114 and 115 each generates a "0" level signal and the comparator 116 generates a "1" level signal, so that only the transistor 128 is turned on and a voltage $V_3$ ($V_3 > V_4$) produced by dividing the supply voltage $V_P$ through the resistors 130 and 133 as the required reference voltage $V_S$.

When the output value of the latch circuit 111 assumes a value intermediate the preset values $S_1$ and $S_2$, the comparator 114 generates a "0" level signal and the comparators 115 and 116 each generate a "1" level signal, so that only the transistor 127 is turned on and a voltage $V_2$ ($V_2 > V_3$) produced by dividing the supply voltage $V_P$ through the resistors 130 and 132 is generated as the required reference voltage $V_S$.

When the output value of the latch circuit 111 exceeds the preset value $S_1$, the comparators 114 to 116 each generates a "1" level signal so that only the transistor 126 is turned on and a voltage $V_1$ ($V_1 > V_2$) produced by dividing the supply voltage $V_P$ through the resistors 130 and 131 as the required reference voltage $V_S$.

In this way the four different values of the reference value $V_S$ can be selectively generated in response to the output voltage of the latch circuit 111 and consequently whether the air-fuel ratio A/F is greater or smaller than the stoichiometric air-fuel ratio ST can be discriminated satisfactorily in the same manner as the previously-mentioned embodiment.

Figure 5:
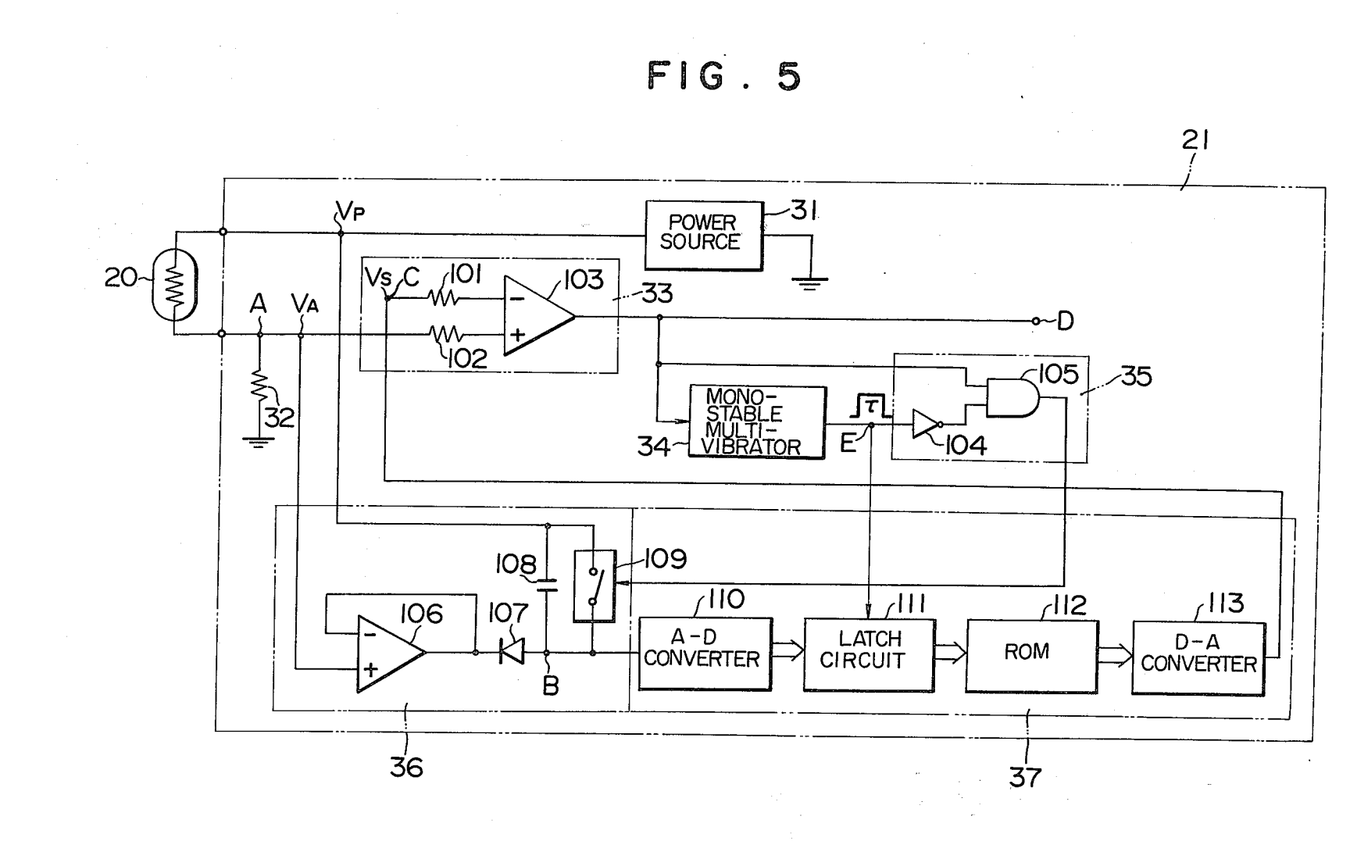
FIG. 5 is a circuit diagram showing a first embodiment of the invention.
Figure 9:
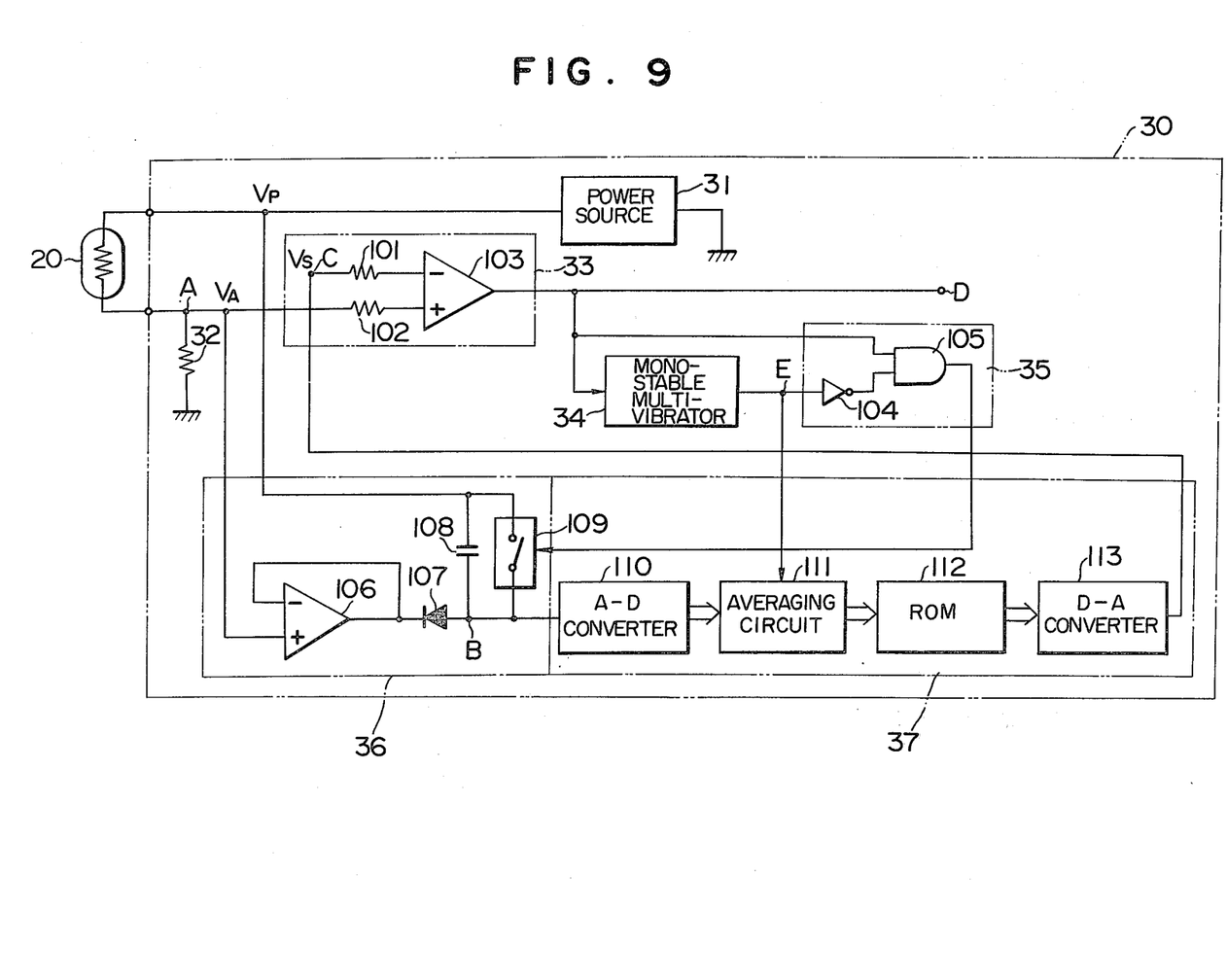
FIG. 9 is a circuit diagram showing a third embodiment of the invention.

Further, while, in the first embodiment of FIG. 5, the reference voltage $V_S$ is changed each time the voltage $V_A$ attains a minimum value, it is possible to change the reference voltage in response to the average value of the minimum values of the voltage $V_A$ as in the case of the third embodiment shown in FIG. 9. The third embodiment differs from the first embodiment in that the reference voltage generating circuit 37 includes an averaging circuit 111. The averaging circuit 111 will now be described in detail with reference to FIG. 10. The averaging circuit 111 is in the form of a digital circuit for operating on binary digital signals and it comprises latch circuits 121 and 122, an adder circuit 123, a register 124, a divider circuit 125, a counter 126, a constant setting circuit 127 and a comparator 128.

Figure 10:
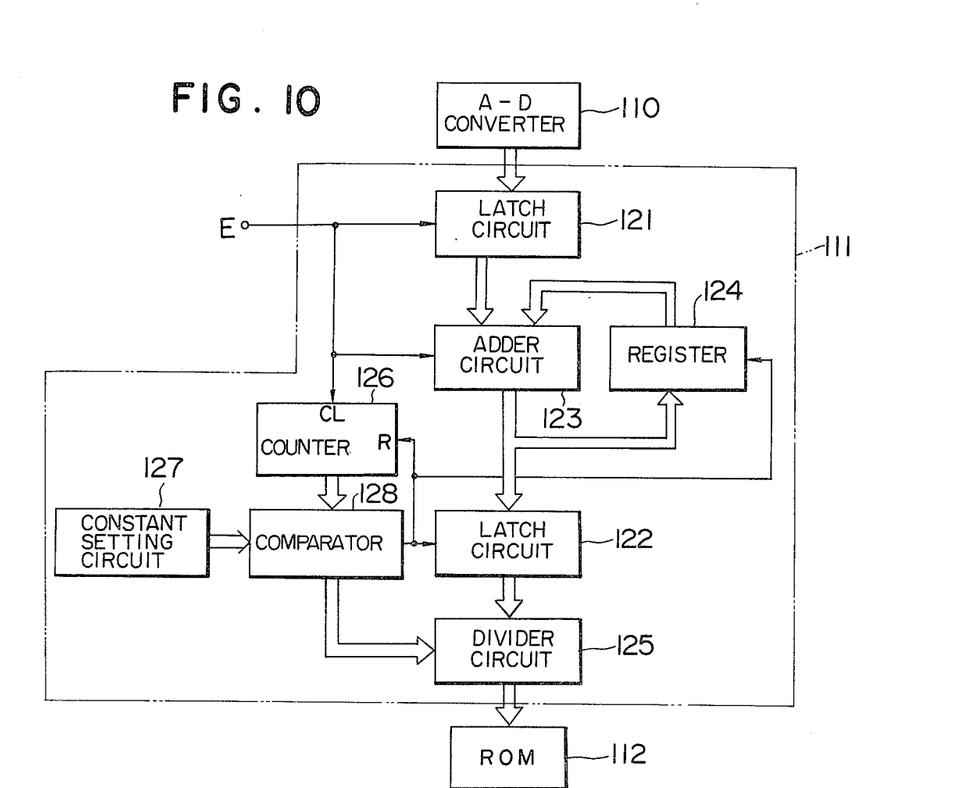
FIG. 10 is a circuit diagram showing in detail the averaging circuit shown in FIG. 10.

When a strobe signal is applied to the latch circuit 121 from the terminal E of the monostable multivibrator 34, the latch circuit 121 reads in the output value of the A-D converter 110 and then applies the same to the adder circuit 123. The register 124 is adapted to temporarily store the output value of the adder circuit 123 and consequently the previous addition output is applied to the adder circuit 123 when the next addition is performed.

The strobe signal from the terminal E is also applied to the adder circuit 123 so that the output values of the latch circuit 121 and the register 124 are added in the adder circuit 123 and the resulting sum is applied to the latch circuit 122.

The counter 126 counts the strobe signals from the terminal E and the resulting count value is applied to the comparator 128. The comparator 128 compares the count value of the counter 126 with an average number of times N preset into the constant setting circuit 127, so that when the two values become equal to each other, a strobe signal is generated and the register 124 and the counter 126 are reset. Simultaneously, the strobe signal is applied to the latch circuit 122 to apply the output value of the adder circuit 123 to the divider circuit 125 and the average number N is also applied to the divider circuit 125.

In this way a value M corresponding to the sum of the minimum peak voltage values at the junction A for N times is applied to the dividend input terminal of the divider circuit 125 and the value N is applied to the divisor input terminal. The divider circuit 125 divides the value M by the value N and produces an average minimum peak voltage value. In this way the minimum peak voltage values at the junction A are averaged and the resulting average minimum peak voltage value is applied to the ROM 112.

With the construction described above, the electric resistance value of the air-fuel ratio sensor 20 changes in response to the gas composition, particularly the oxygen content of the exhaust gases from the engine 10. The exhaust gas composition varies in response to the air-fuel ratio A/F of the mixture supplied to the engine 10 from the mixture feed unit 12 and consequently the elelctric resistance value Re of the air-fuel ratio sensor 20 varies in response to the air-fuel ratio A/F as shown in FIG. 1.

In other words, the air-fuel ratio sensor 20 has a lean resistance value L when the air-fuel ratio A/F is greater than the stoichiometric air-fuel ratio ST (14.7) and it has a rich resistance value R when the air-fuel ratio A/F is smaller than the stoichiometric ratio ST.

Figure 11:
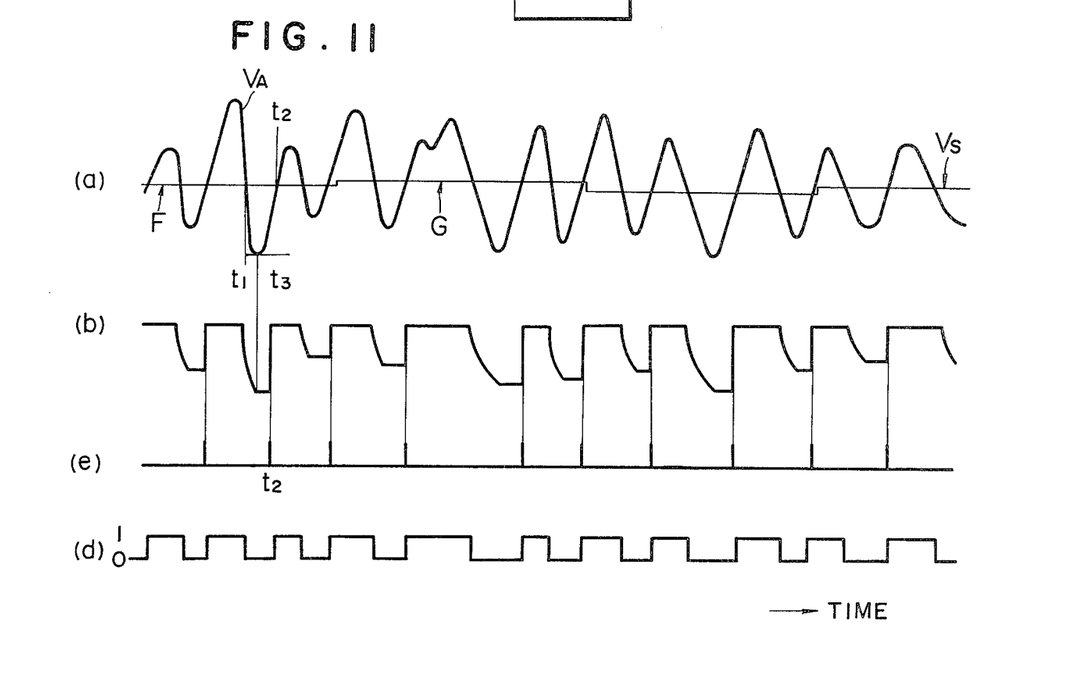
FIG. 11 is a graph useful for explaining the operation of the third embodiment.

The voltage $V_A$ at the junction A is dependent on the electric resistance value Re of the air-fuel ratio sensor 20 and it varies in response to variations of the air-fuel ratio A/F as shown by a curve $V_A$ in (a) of FIG. 11.

Thus, when the reference voltage $V_S$ generated from the voltage generating circuit 37 is at the level indicated at F in (a) of FIG. 11, as long as the voltage $V_A$ at the junction A is higher than the reference voltage $V_S$, the comparator circuit 33 generates a "1" level rich signal as shown in (d) of FIG. 11. When the voltage $V_A$ becomes lower than the reference voltage $V_S$ at a time $t_1$, the output of the comparator circuit 33 becomes to be from the "1" level to the "0" level. As a result, the output signal of the AND gate 105 also becomes to be of the "0" level, so that the analog switch 109 is turned off and the capacitor 108 starts to charge.

Consequently, the voltage $V_B$ at the terminal B of the capacitor 108 decreases in response to the output voltage of the buffer amplifier 106 or the voltage $V_A$ at the junction A, so that when a minimum peak value is attained the minimum peak value is detected and held as shown at a time $t_3$ in (b) of FIG. 11.

When the voltage $V_A$ again becomes higher than the reference voltage $V_S$ at a time $t_2$, the output of the comparator circuit 33 becomes from the "0" level to the "1" level. In response to the transition of the signal the monostable multivibrator 34 generates a "1" level strobe signal $\tau$ so that the current voltage $V_B$ at this time at the terminal B of the capacitor 108 or the minimum peak voltage is applied to the averaging circuit 111 through the A-D converter 110.

In the averaging circuit 111 the minimum peak voltage value is added N times, e.g., three times in the adder circuit 123 and the resulting sum is divided by N (=3) in the divider circuit 125 and an average minimum peak voltage value $V_{min}$ is produced.

The voltage value $V_{min}$ is applied to the ROM 112 so that the voltage value $V_{min}$ is modulated according to the functional relation shown in FIG. 7 and it is generated as the desired reference voltage $V_S$ from the ROM 112. As a result, the new reference voltage $V_S$ is applied to the comparator circuit 33 through the D-A converter 113 and the reference voltage $V_S$ is raised to a level G in (a) of FIG. 11.

When the strobe signal of the monostable multivibrator 34 shown in (e) of FIG. 11 becomes to be of the "0" level, the two input terminals of the AND gate 105 each receives a "1" level signal so that the AND gate 105 generates a "1" level signal and the analog switch 109 is turned on, thus discharging the charge on the capacitor 108. Thereafter, the respective circuits repeat the above-mentioned operations.

With the third embodiment, the reference voltage values are preset according to the functional relation shown in FIG. 7 in correspondence with the average minimum peak values $V_{min}$ of the voltage $V_A$ and the reference voltage values are preset so that the reference voltage $V_S$ is decreased with a decrease in the average minimum peak value $V_{min}$ of the voltage $V_A$.

While, in the embodiment described above, the averaging circuit 111 is used to produce the average of N peak values, it is possible to construct so that each time a strobe signal is generated at the terminal E the average of N peak values just before the generation of the signal is produced.

Further, with the above-described three embodiments, when the voltage $V_A$ at the junction A (the voltage across the reference voltage 32) attains a minimum peak value, the voltage is held by the sample-and-hold circuit 36 and the reference voltage $V_S$ is changed.

However, it is possible to reverse the connection of the reference resistor 32 and the air-fuel ratio sensor 20 so as to sample the peak value of a voltage generated across the air-fuel ratio sensor 20 and indicative of a large air-fuel ratio. In this case, it is necessary to arrange so that when the voltage $V_A$ across the air-fuel ratio sensor 20 reaches a maximum peak value, the voltage is detected and the reference voltage $V_S$ is changed according to the detected voltage.

While the above-described three embodiments have been described as incorporated in a system for controlling the air-fuel ratio of mixtures in the intake system of engines, the embodiments can be incorporated in a so-called exhaust system air-fuel ratio control system in which the amount of additional air supplied to the exhaust system is controlled by the air-fuel ratio sensor 20.

What is claimed is:

1. An air-fuel ratio detecting system for internal combustion engines comprising:
    oxygen detecting means disposed in an exhaust passage of an internal combustion engine for detecting a presence and an absence of oxygen, said oxygen detecting means exhibiting a low resistance and a high resistance in response to said absence and said presence of oxygen respectively;
    resistor means connected in series with said oxygen detecting means;
    voltage supplying means for supplying a series circuit of said oxygen detecting means and said resistor means with a voltage so that a first and a second voltages are developed at a junction between said oxygen detecting means and said resistor means in response to said low resistance and said high resistance of said oxygen detecting means, respectively;
    sampling means for sampling a peak value of at least one of said first and second voltages during a sampling period;
    reference establishing means for establishing a reference value related to said sampling peak value of said at least one of said first and second voltages; and
    comparing means for comparing said first and second voltages with said reference value.

2. An air-fuel ratio detecting system according to claim 1, wherein said reference establishing means includes a memory in which a desired relation between said sampled peak value and said reference value is programmable.

3. An air-fuel ratio detecting system according to claim 1, wherein said sampling means samples said at least one of said first and second voltages at any preset time.

4. An air-fuel ratio detecting system for internal combustion engines comprising:
    oxygen detecting means disposed in an exhaust passage of an internal combustion engine for detecting a presence and an absence of oxygen, said oxygen detecting means exhibiting a low resistance and a high resistance in response to said absence and said presence of oxygen, respectively;
    resistor means connected in series with said oxygen detecting means;
    voltage supplying means for supplying a series circuit of said oxygen detecting means and said resistor means with a voltage to that a first voltage and a second voltage and a second voltage are developed at a junction between said oxygen detecting means and said resistor means in response to said low resistance and said high resistance of said oxygen detecting means, respectively;
    sampling means for sampling a peak value of at least one of said first and second voltages during a sampling period;
    reference establishing means for establishing a reference voltage related to said sampled peak value of said at least one of said first and second voltages, said reference establishing means including an averaging means for averaging outputs of said sampling means and generating said reference voltage in accordance with a value resulting from the averaging; and
    comparing means for comparing said first and second voltages with said reference voltage.

5. An air-fuel ratio sensor system according to claim 4, wherein said averaging means includes an adder for adding sampled values and a divider for dividing the sum of sampled values by the number of sampling times to produce average sampled values.

6. An air-fuel ratio detecting system according to claim 4, wherein said averaging means includes an integrator for integrating samples values and said averaging means averages values integrated by said integrator.

7. An air-fuel ratio detecting system according to claim 1 or 3, wherein said reference establishing means includes a plurality of level comparators, each level comparator comparing the level of sampled sensor output, to produce an appropriate reference voltage selected from more than two predetermined reference voltages in accordance with the results of comparison by said plurality of comparators.

8. An air-fuel ratio detecting system for internal combustion engines comprising:
    means for generating an oxygen signal related to the amount of oxygen in the gas in an exhaust passage of an internal combustion engine;
    means for sampling a peak value of said oxygen signal during a sample period;
    reference establishing means for establishing a reference value related to said sample peak value; and
    means for comparing said oxygen signal with said reference value.

9. An air-fuel ratio detecting system according to claim 8, wherein said sampling means samples said oxygen signal over a period which varies with engine conditions.

10. An air-fuel ratio detecting system according to claim 8 or 9, wherein said reference establishing means includes a plurality of level comparators, each level comparator comparing the level of sampled sensor output, to produce an appropriate reference voltage selected from more than two predetermined reference voltages in accordance with the results of comparison by said plurality of comparators.

11. An air-fuel ratio detecting system according to claim 8, wherein said reference establishing means includes a memory in which a desired relation between said sampled peak value and said reference value is programmable.

12. An air-fuel ratio detecting system for internal combustion engines comprising:
    oxygen detecting means disposed in an exhaust passage of an internal combustion engine for detecting a presence and an absence of oxygen, said oxygen detecting means exhibiting a low resistance and a high resistance in response to said absence and said presence of oxygen respectively;

resistor means connected in series with said oxygen detecting means;

voltage supplying means for supplying a series circuit of said oxygen detecting means and said resistor means with a constant voltage so that a first and a second voltages are developed at a junction between said oxygen detecting means and said resistor means in response to said low resistance and said high resistance of said oxygen detecting means, respectively;

sampling means for sampling a peak value of at least one of said first and second voltages during a sampling period;

reference establishing means for establishing a reference value related to said sampling peak value of said at least one of said first and second voltages; and comparing means for comparing said first and second voltages with said reference value.

13. An air-fuel ratio detecting system according to claim 1, 4, 8 or 12 wherein said sampling means includes first means for activating said sampling means when an output of said comparing means changes state in a predetermined first direction.

14. An air-fuel ratio detecting system according to claim 13 wherein:

said sampling means includes a capacitor; and said first activating means includes an electronic switch connected in parallel with said capacitor, said switch opening in response to said comparing means output.

15. An air-fuel ratio detecting system according to claim 13 further comprising:

second means for activating said reference establishing means when said comparing means output changes state in a second direction opposite said first direction; and means for initializing said sampling means a predetermined time after said comparing means output changes to said second state.

16. An air-fuel detecting system according to claim 15 wherein said second activating means includes a monostable multivibrator, responsive to said comparing means output changing to said second state, and said initializing means includes an AND-gate having inputs responsive to said comparing means output and an output of said monostable multivibrator, said first activating means being responsive to said AND-gate output.

17. An air-fuel ratio detecting system according to claim 1, 4, 8 or 12 wherein:

said sampling means includes a capacitor and an electronic switch connected in parallel with said capacitor; and said detecting system further comprises:

a monostable multivibrator for producing a pulse when an output of said comparing means switches from a second state to a first state, said reference establishing means being responsive to said pulse, and an AND-gate having one input responsive to said comparing means, another input responsive to said pulse, and an output, said switch being responsive to said AND-gate output, said AND-gate producing a signal opening said switch extending from said comparing means output changing to said second state to a predetermined time after said comparing means output changes back to said first state.

18. An air-fuel ratio detecting system according to claim 1, 4, 8 or 12 wherein said reference establishing means including means for converting said sampling peak value to a digital number, means for determining said reference value in digital form from said digital number, and means for converting said digital form into an analog form.

* * * * *